(12) United States Patent
Kawano

(10) Patent No.: US 8,734,329 B2
(45) Date of Patent: May 27, 2014

(54) CAPSULE MEDICAL DEVICE GUIDING SYSTEM AND MAGNETIC FIELD GENERATING DEVICE

(75) Inventor: Hironao Kawano, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/558,508

(22) Filed: Jul. 26, 2012

(65) Prior Publication Data

US 2013/0041217 A1 Feb. 14, 2013

Related U.S. Application Data

(63) Continuation of application No. PCT/JP2012/051354, filed on Jan. 23, 2012.

(30) Foreign Application Priority Data

Jan. 28, 2011 (JP) ................................. 2011-016124

(51) Int. Cl.
*A61B 1/00* (2006.01)
(52) U.S. Cl.
CPC ................................. *A61B 1/00158* (2013.01)
USPC .......................................... 600/114; 600/118
(58) Field of Classification Search
CPC .................................................... A61B 1/00158
USPC .......................................... 600/114, 117, 118
See application file for complete search history.

(56) References Cited

U.S. PATENT DOCUMENTS

| 7,173,507 B2 * | 2/2007 | Ries ............................... 335/299 |
| 7,182,089 B2 * | 2/2007 | Ries ............................... 128/899 |
| 7,637,864 B2 * | 12/2009 | Yokoi et al. ................... 600/114 |

(Continued)

FOREIGN PATENT DOCUMENTS

| DE | 10 2009 007 513 A1 | 8/2010 |
| EP | 2 143 371 A1 | 1/2010 |

(Continued)

OTHER PUBLICATIONS

Japanese Office Action dated Sep. 11, 2012 from corresponding Japanese Patent Application No. JP 2012-534469 together with an English language translation.

(Continued)

*Primary Examiner* — John P Leubecker
(74) *Attorney, Agent, or Firm* — Scully, Scott, Murphy & Presser, P.C.

(57) ABSTRACT

A guiding system includes a capsule medical device including a permanent magnet; a magnetic field generating unit to generate a magnetic field to the magnet to guide the capsule, and change a direction of the magnetic field in a three-dimensional space; and a control unit to control the magnetic field generated by the generating unit. Where the capsule is located on a liquid surface, the control unit generates a first magnetic field such that a plane, which is parallel to a vertical axis and in which a magnetic field including a rotating magnetic field where a magnetic field is rotated on the plane is generated, pivots about the vertical axis at a predetermined period and a second magnetic field for generating a magnetic attracting force for moving the magnet vertically downward to submerge the capsule in the liquid, the first and second magnetic fields being applied at a same time.

18 Claims, 14 Drawing Sheets

(56) References Cited

U.S. PATENT DOCUMENTS

| | | |
|---|---|---|
| 8,241,206 B2 * | 8/2012 | Kawano .................. 600/117 |
| 8,317,682 B2 * | 11/2012 | Kawano et al. ............ 600/118 |
| 2003/0018280 A1 | 1/2003 | Lewkowicz et al. |
| 2005/0085960 A1 | 4/2005 | Uchiyama et al. |
| 2007/0197872 A1 * | 8/2007 | Uchiyama et al. ......... 600/117 |
| 2007/0221233 A1 | 9/2007 | Kawano et al. |
| 2007/0260105 A1 | 11/2007 | Uchiyama et al. |
| 2008/0306340 A1 * | 12/2008 | Uchiyama et al. ......... 600/117 |
| 2010/0010305 A1 | 1/2010 | Kawano |
| 2010/0307517 A1 * | 12/2010 | Kawano et al. ............ 128/899 |
| 2012/0022328 A1 | 1/2012 | Reinschke |
| 2012/0265015 A1 * | 10/2012 | Kawano et al. ............ 600/118 |

FOREIGN PATENT DOCUMENTS

| | | |
|---|---|---|
| JP | 2004-529718 A | 9/2004 |
| JP | 2005-58430 A | 3/2005 |
| JP | 2006-263167 A | 10/2006 |
| JP | 2010-17555 A | 1/2010 |
| JP | 2010-142388 A | 7/2010 |
| WO | WO 2007/077922 A1 | 7/2007 |

OTHER PUBLICATIONS

International Search Report PCT/JP2012/051354 dated Apr. 17, 2012.

International Search Report PCT/JP2012/051354 dated Apr. 17, 2012 together with an English language translation.

Written Opinion PCT/JP2012/051354 dated Apr. 17, 2012.

English language abstract only of International Publiation No. WO 02095351 A2 published Nov. 28, 2002.

Extended Supplementary European Search Report dated Jan. 23, 2014 in corresponding European Patent Application No. 12738850.2.

* cited by examiner

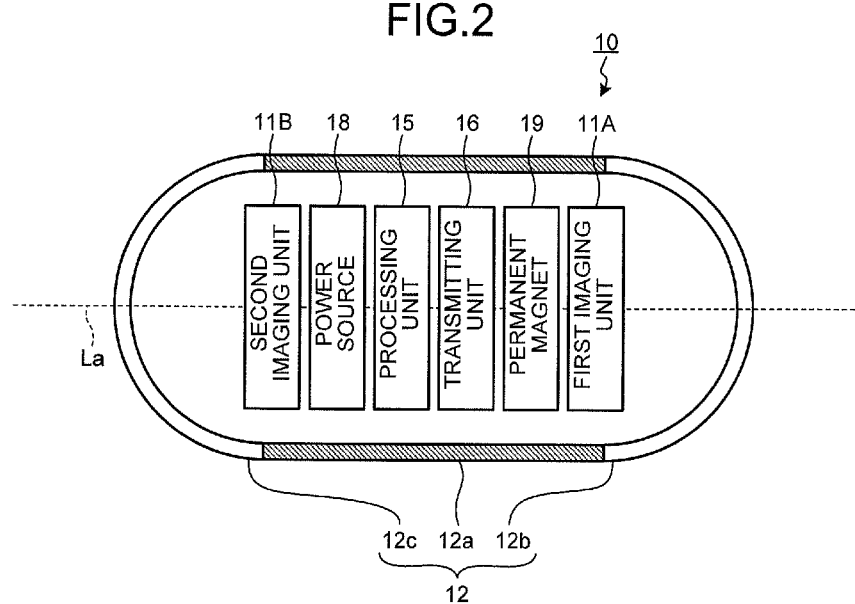
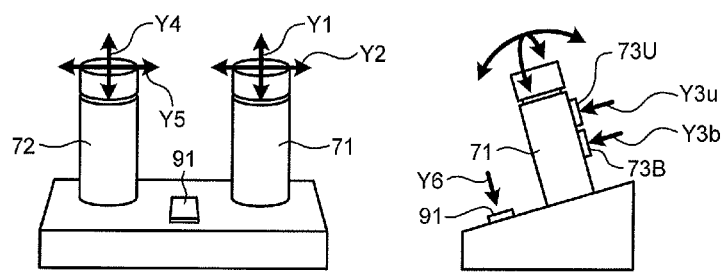

CAPSULE MEDICAL DEVICE GUIDING SYSTEM AND MAGNETIC FIELD GENERATING DEVICE

CROSS REFERENCES TO RELATED APPLICATIONS

This application is a continuation of PCT international application Ser. No. PCT/JP2012/051354 filed on Jan. 23, 2012 which designates the United States, incorporated herein by reference, and which claims the benefit of priority from Japanese Patent Applications No. 2011-016124, filed on Jan. 28, 2011, incorporated herein by reference.

BACKGROUND OF THE INVENTION

1. Field of the Invention

The present invention relates to a capsule medical device guiding system for guiding a capsule medical device, which is introduced into a liquid in a subject and equipped with a permanent magnet, and a magnetic field generating device for generating a magnetic field for the capsule medical device.

2. Description of the Related Art

Conventionally, in the field of endoscopes, capsule endoscopes that include an imaging function and a wireless communication function in a capsule-shaped casing having a size introducible into an alimentary canal of a subject such as a patient have been developed. Such a capsule endoscope is swallowed through the mouth of a subject, and then is moved in the alimentary canal through peristaltic movement. The capsule endoscope sequentially acquires images (hereinafter, also referred to as in-vivo images) of internal organs of a subject, and wirelessly transmits the acquired in-vivo images to a receiving device outside the subject in sequence, during a time period until the capsule endoscope is excreted to the outside of the subject after being introduced into the alimentary canal of the subject.

The in-vivo images captured by the capsule endoscope are input to an image display unit via the receiving device. The image display unit displays the input in-vivo images on a display in the form of still images or moving images. A user such as a doctor or a nurse observes various in-vivo images of the subject displayed on the image display unit, and examines the internal organs of the subject through observation of the in-vivo images.

Further, in recent years, guiding systems for guiding (hereinafter, referred to as magnetically guiding) a capsule endoscope in a subject by using a magnetic force are being suggested. In general, in such a guiding system, the capsule endoscope further includes a permanent magnet within a capsule-shaped casing, and an image display unit displays various in-vivo images sequentially captured by the capsule endoscope within the subject in real time. The guiding system of the capsule endoscope applies a magnetic field for the capsule endoscope within the subject, and magnetically guides the capsule endoscope within the subject to a desired location due to a magnetic attracting force received by the applied magnetic field. The user manipulates magnetic guidance of the capsule endoscope by using a manipulation input unit of the system while referring to the in-vivo images displayed on the image display unit.

For example, a magnetic guiding system for a capsule endoscope which applies a rotating magnetic field for rotating about a horizontal axis center of a long axis of the capsule endoscope and reciprocally rotates the capsule endoscope about the horizontal axis center of the long axis, in order to submerge the capsule endoscope located on a liquid surface into a liquid against a surface tension of the liquid surface has been suggested (see, for example, Japanese Laid-open Patent Publication No. 2010-017555). Further, a technology of applying a magnetic field for pivoting a capsule endoscope in a long axis direction of the capsule endoscope while rotating the capsule endoscope about a long axis of the capsule endoscope has been suggested (see, for example, Japanese Laid-open Patent Publication No. 2005-058430).

SUMMARY OF THE INVENTION

A capsule medical device guiding system according to an aspect of the present invention includes: a capsule medical device including a permanent magnet and introduced into a liquid in a subject; a magnetic field generating unit configured to generate a magnetic field applied to the permanent magnet to guide the capsule medical device, and change a direction of the generated magnetic field in a three-dimensional space; and a control unit configured to control the magnetic field generated by the magnetic field generating unit, wherein in a state where the capsule medical device is located on a liquid surface of the liquid, the control unit controls to generate a first magnetic field such that a plane, which is parallel to a vertical axis and in which a magnetic field including a rotating magnetic field where a magnetic field is rotated on the plane is generated, pivots about the vertical axis at a predetermined period and to generate a second magnetic field for generating a magnetic attracting force for moving the permanent magnet vertically downward to submerge the capsule medical device in the liquid, and controls such that the first and second magnetic fields are applied at a same time.

A capsule medical device guiding system according to another aspect of the present invention includes: a capsule medical device including a permanent magnet, introduced into a liquid of a subject, and having substantially a same density as a density of a liquid introduced into the subject; a magnetic field generating unit configured to generate a magnetic field applied to the permanent magnet to guide the capsule medical device, and change a direction of the generated magnetic field in a three-dimensional space; and a control unit configured to control the magnetic field generated by the magnetic field generating unit, wherein in a state where the capsule medical device is located on a liquid surface of the liquid, the control unit controls to generate a first magnetic field such that a plane, which is parallel to a vertical axis and in which a magnetic field including a rotating magnetic field where a magnetic field is rotated on the plane is generated, pivots about the vertical axis at a predetermined period and to generate a second magnetic field for generating a magnetic attracting force for moving the permanent magnet vertically downward to submerge the capsule medical device in the liquid, and controls such that the first and second magnetic fields are applied at a same time.

A magnetic field generating device for generating a magnetic field for a capsule medical device including a permanent magnet according to still another aspect of the present invention includes: a magnetic field generating unit configured to generate a magnetic field applied to the permanent magnet to guide the capsule medical device, and change a direction of the generated magnetic field in a three-dimensional space; and a control unit configured to control the magnetic field generated by the magnetic field generating unit, wherein in a state where the capsule medical device is located on a liquid surface of the liquid, the control unit controls to generate a first magnetic field such that a plane, which is parallel to a vertical axis and in which a magnetic field including a rotating magnetic field where a magnetic field is rotated on the plane is generated, pivots about the vertical axis at a predetermined period and to generate a second magnetic field for generating a magnetic attracting force for moving the permanent magnet vertically downward to submerge the capsule medical device in the liquid, and controls such that the first and second magnetic fields are applied at a same time.

A capsule medical device guiding system according to still another aspect of the present invention includes: a capsule medical device including a permanent magnet and introduced into a liquid in a subject; a magnetic field generating unit configured to generate a magnetic field applied to the permanent magnet to guide the capsule medical device, and change a direction of the generated magnetic field in a three-dimensional space; and a control unit configured to control the magnetic field generated by the magnetic field generating unit, wherein a gravity center of the capsule medical device is disposed at a location moved in a direction different from a magnetization direction of the permanent magnet from a geometric center of the capsule medical device, and in a state where the capsule medical device is located on a liquid surface of the liquid, the control unit controls such that the magnetic field generating unit simultaneously applies a first magnetic field, a direction of which is changed from a state where the gravity center of the capsule medical device is located below the geometric center to a state where the gravity center of the capsule medical device is located above the geometric center, and a second magnetic field for moving the permanent magnet to a lower side to generate a magnetic attracting force for submerging the capsule medical device into the liquid.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 2 is a sectional schematic diagram illustrating an exemplary configuration of a capsule endoscope illustrated in FIG. 1;

FIGS. 3A and 3B illustrate views of an example of a manipulation input unit used in the capsule medical device guiding system according to the first embodiment;

DETAILED DESCRIPTION OF THE PREFERRED EMBODIMENTS

Figure 1:
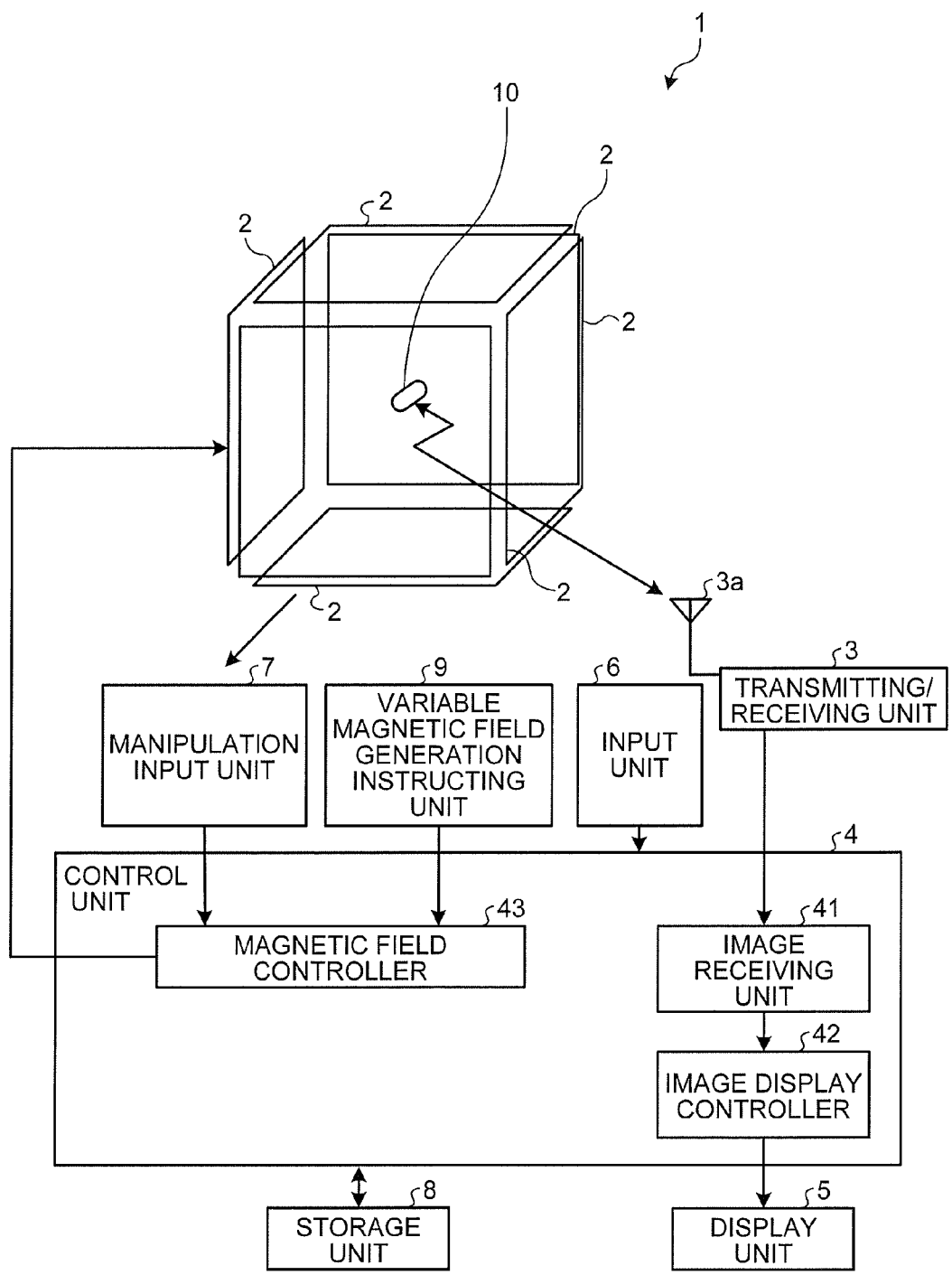
FIG. 1 is a schematic diagram illustrating an entire configuration of a capsule medical device guiding system according to a first embodiment.

Hereinafter, in regard to a capsule medical device guiding system according to an embodiment of the present invention, a guiding system for a capsule endoscope which uses a capsule endoscope introduced into an oral of a subject and floating in a liquid accumulated on a stomach of the subject will be described as an example. Meanwhile, the present invention is not limited thereto, but may use various capsule medical devices such as, for example, a capsule endoscope moving in a lumen from the gullet of a subject along the anal or a capsule endoscope introduced from the anal together with an isotonic solution. Further, in the description of the drawings, the same reference numerals denote the same parts.

First Embodiment

First, a first embodiment will be described. FIG. 1 is a schematic diagram illustrating an entire configuration of a capsule medical device guiding system according to a first embodiment of the present invention.

As illustrated in FIG. 1, a capsule medical device guiding system 1 according to the first embodiment includes a capsule endoscope 10 which is a capsule medical device swallowed through the mouth of a subject to be introduced into a body cavity in the subject and configured to communicate with an external device, a magnetic field generating unit 2 provided around the subject and configured to generate a three-dimensional magnetic field, a transmitting/receiving unit 3 configured to perform a wireless communication with the capsule endoscope 10 and configured to receive a wireless signal containing an image captured by the capsule endoscope 10 and transmit a manipulation signal for the capsule endoscope 10, a control unit 4 configured to control various constituent elements of the capsule medical device guiding system 1, a display unit 5 configured to display and output the image captured by the capsule endoscope 10, an input unit 6 configured to input instruction information for instructing various manipulations in the capsule medical device guiding system 1, a manipulation input unit 7 configured to input guidance instructing information for magnetically guiding the capsule endoscope 10, a storage unit 8 configured to store image information captured by the capsule endoscope 10, and a variable magnetic field generation instructing unit 9 configured to input variable magnetic field instructing information for instructing generation of a variable magnetic field for moving the capsule endoscope 10 restricted to a liquid surface into the liquid.

The capsule endoscope 10 is a capsule medical device configured to acquire an in-vivo image of a subject, and employs an imaging function and a wireless communication function therein. After being introduced into an internal organ of a subject together with a specific liquid through an oral ingestion, the capsule endoscope 10 is moved through the interior of an alimentary canal and is finally excreted to the outside of the subject. The capsule endoscope 10 sequentially captures in-vivo images in the subject, and sequentially wirelessly transmits the obtained in-vivo images to the external transmitting/receiving unit 3. Further, the capsule endoscope 10 employs a magnetic body such as a permanent magnet therein. The capsule endoscope 10 drifts in the liquid introduced into an interior of an alimentary canal (for example, an interior of a stomach) of the subject, and is moved in the liquid while being magnetically guided by the external magnetic field generating unit 2.

FIG. 2 is a sectional schematic diagram illustrating an exemplary configuration of the capsule endoscope illustrated in FIG. 1. As illustrated in FIG. 2, the capsule endoscope 10 includes a first imaging unit 11A, a second imaging unit 11B, a capsule-shaped casing 12, a processing unit 15, a transmitting unit 16, a power source 18, and a permanent magnet 19. The first imaging unit 11A and the second imaging unit 11B have an illumination system such as an LED, an optical system such as a condenser lens, and an imaging element such as a CMOS image sensor or a CCD, respectively, and capture images of a subject in different imaging directions. The capsule-shaped casing 12 is an external body formed to have a size easily introducible into the interior of an alimentary canal of a subject, and is configured such that opposite opening ends of a substantially opaque colored tubular casing 12a are blocked by dome-shaped transparent casings 12b and 12c. For example, when the capsule endoscope 10 is a two-lens capsule medical device for capturing a front side and a rear side in a direction of a long axis La, the optical axes of the first imaging unit 11A and the second imaging unit 11B are substantially parallel to or substantially the same as the long axis La which is a lengthwise center axis of the capsule-shaped casing 12. The processing unit 15 performs various processing such as noise removing processing or amplifying processing for various images captured by the first imaging unit 11A and the second imaging unit 11B. The transmitting unit 16 generates a wireless signal obtained by modulating an image signal containing various images processed by the processing unit 15, and transmits the wireless signal to the external transmitting/receiving unit 3 via an antenna (not illustrated). The power source 18 has an accumulating unit such as a button type battery or a capacitor and a switch unit such as a magnetic switch, and supplies electric power to the constituent elements of the capsule endoscope 10. The permanent magnet 19 is for enabling a magnetic guidance by the magnetic field generating unit 2, and is fixedly disposed within the capsule-shaped casing 12.

The magnetic field generating unit 2 is for magnetically guiding the capsule endoscope 10 in the subject. The magnetic field generating unit 2 is realized by using, for example, a plurality of coils, and generates a guiding magnetic field by using electric power supplied by an electric power supply unit (not shown). The magnetic field generating unit 2 applies the generated guiding magnetic field to a magnetic body in the capsule endoscope 10, and magnetically captures the capsule endoscope 10 through an operation of the guiding magnetic field. The magnetic field generating unit 2 may change a direction of the generated magnetic field in a three-dimensional space. The magnetic field generating unit 2 changes a magnetic field direction of the guiding magnetic field applied to the capsule endoscope 10 in the subject to control a three-dimensional posture of the capsule endoscope 10 in the subject.

The transmitting/receiving unit 3 includes a plurality of antennas 3a, and receives in-vivo images of the subject from the capsule endoscope 10 via the plurality of antennas 3a. The transmitting/receiving unit 3 sequentially receives wireless signals from the capsule endoscope 10 via the plurality of antennas 3a. The transmitting/receiving unit 3 selects an antenna having the highest received magnetic field intensity among the plurality of antennas 3a, and performs demodulating processing on the wireless signals from the capsule endoscope 10 received via the selected antenna. Accordingly, the transmitting/receiving unit 3 extracts image data by the capsule endoscope 10, that is, in-vivo image data of the subject from the wireless signal. The transmitting/receiving unit 3 transmits image signals containing the extracted in-vivo image data to the control unit 4.

The control unit 4 controls operations of the magnetic field generating unit 2, the transmitting/receiving unit 3, the display unit 5, and the storage unit 8, and controls input/output of signals between the constituent elements. The control unit 4 controls the storage unit 8 to store the in-vivo image group of the subject acquired from the transmitting/receiving unit 3. The control unit 4 includes an image receiving unit 41 configured to sequentially acquire the in-vivo images sequentially received by the transmitting/receiving unit 3, an image display controller 42 configured to display the in-vivo images sequentially received by the transmitting/receiving unit 3 on the display unit 5 in real time, and a magnetic field controller 43 configured to control the magnetic field generating unit 2 to guide the capsule endoscope 10. The magnetic field controller 43 controls an amount of current flowed to the magnetic field generating unit 2, and controls the magnetic field generating unit 2 to generate a guiding magnetic field necessary for magnetic guidance of the capsule endoscope 10 according to a magnetic guidance direction and a magnetic guidance location based on guidance instructing information.

The display unit 5 is realized by using various displays such as a liquid crystal monitor, and displays various information instructed to display by the control unit 4. In detail, the display unit 5 displays, for example, an in-vivo image group of the subject captured by the capsule endoscope 10, based on the control of the image display controller 42 in the control unit 4. Further, the display unit 5 displays reduced images of the in-vivo images selected or marked through an input manipulation of the input unit 6 among the in-vivo image group, and patient information and examination information of the subject.

The input unit 6 is realized by using an input device such as a keyboard and a mouse, and inputs various information to the control unit 4 according to an input manipulation by a user such as a doctor. The various information input to the control unit 4 by the input unit 6 may include, for example, instruction information instructed to the control unit 4, and patient information and examination information of the subject. Further, the patient information of the subject is specific information specifying the subject, and includes, for example, a patent name, a patent ID, a birth date, a gender, and an age of the subject. Further, the examination information of the subject is specific information specifying an examination for introducing the capsule endoscope 10 into the interior of the alimentary canal of the subject and observing the interior of the alimentary canal, and includes, for example, an examination ID and an examination date.

Guidance instructing information for magnetically guiding the capsule endoscope 10 is input to the manipulation input unit 7. The manipulation input unit 7 inputs guidance instructing information for magnetically guiding the capsule endoscope 10, which is a magnetic guidance manipulated object, to the control unit 4. The guidance instructing information is for instructing a posture or a location of the capsule endoscope 10. The magnetic field controller 43 generates a magnetic field corresponding to the guidance instructing information in the magnetic field generating unit 2. The manipulation input unit 7 has configurations including a joystick, various buttons, and various switches, and inputs the guidance instructing information to the control unit 4 as the joystick is manipulated by a user.

For example, as illustrated in FIG. 3A, the manipulation input unit 7 is configured as a manipulation input unit including two joysticks 71 and 72. The joysticks 71 and 72 are used to three-dimensionally manipulate the capsule endoscope 10 through magnetic guidance, and may be tilted to the upper side, lower side, left side, and right side of the paper. Further, as illustrated in FIG. 3B, an up button 73U and a down button 73B are provided on a rear surface of the joystick 71.

Figure 4:
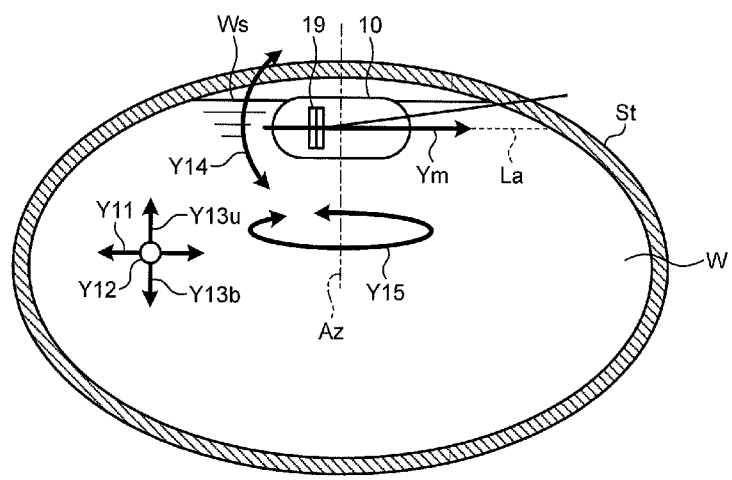
FIG. 4 is a view illustrating magnetization of a permanent magnet of the capsule endoscope illustrated in FIG. 1 and an operation of the capsule endoscope.

As a capsule endoscope magnetically guided in response to tilting manipulations of the joysticks 71 and 72, the capsule endoscope 10, in which the permanent magnet 19 is fixedly disposed to have a magnetization Ym in a direction parallel to the long axis La of the capsule endoscope 10 as illustrated in FIG. 4, will be described as an example. Incidentally, FIG. 4 is a view where the capsule endoscope 10 is viewed from a direction perpendicular to a vertical axis, and exemplifies that the capsule endoscope 10 is located within the stomach St. Further, the density of the capsule endoscope 10 is set to be substantially the same as the density of a liquid W introduced into the subject. FIG. 4 exemplifies that the capsule endoscope 10 is located on the liquid surface Ws of the liquid W.

As indicated by an arrow Y1 illustrated in FIG. 3A, when the joystick 71 is tilted between the rear side of the paper and the front surface of the paper of FIG. 3A, guidance instructing information for guiding the capsule endoscope 10 to the left and right sides of FIG. 4 is input to the control unit 4 as indicated by the arrow Y1 (see FIG. 4). As indicated by an arrow Y2 illustrated in FIG. 3A, when the joystick 71 is tilted to the left and right sides of the paper, guidance instructing information for guiding the capsule endoscope 10 in a direction perpendicular to the paper of FIG. 4 is input to the control unit 4. For example, when the capsule endoscope 10 is located on a point Y12 (see FIG. 4), the capsule endoscope 10 is guided in a direction perpendicular to the paper of FIG. 4 to pass through the point Y12.

As indicated by an arrow Y3u illustrated in FIG. 3B, when the up button 73U is pressed, guidance instructing information for instructing guidance of the capsule endoscope 10 vertically upward is input to the control unit 4 as indicated by an arrow Y13u of FIG. 4. As indicated by an arrow Y3b illustrated in FIG. 3B, when the down Button 73B is pressed, guidance instructing information for instructing guidance of the capsule endoscope 10 vertically downward is input to the control unit 4 as indicated by an arrow Y13b of FIG. 4.

As indicated by an arrow Y4 illustrated in FIG. 3A, when the joystick 72 is tilted between the rear side of the paper and the front surface of the paper of FIG. 3A, guidance instructing information for operating the capsule endoscope 10 such that an end of the capsule endoscope 10 is shaken to the upper and lower sides of the paper as a neck is shaken is input to the control unit 4 as indicated by the arrow Y14 (see FIG. 4). As indicated by an arrow Y5 illustrated in FIG. 3A, when the joystick 72 is tilted to the left and right sides of the paper, guidance instructing information for guiding the capsule endoscope 10 to rotate about a vertical axis Az as illustrated in an arrow Y15 of FIG. 4 is input to the control unit 4.

The storage unit 8 is realized by using a storage medium, such as flash memory or a hard disk, for rewritably preserving information. The storage unit 8 stores various information instructed to store by the control unit 4, and delivers information instructed to be read out by the control unit 4 in the stored information to the control unit 4. Further, the various information stored by the storage unit 8 may include, for example, various image data of the in-vivo image group of the subject captured by the capsule endoscope 10, data of the in-vivo images selected through the input manipulation of the input unit 6 among the in-vivo images displayed on the display unit 5, and input information by the input unit 6 such as patient information of the subject.

The variable magnetic field generation instructing unit 9 includes a variable magnetic field button 91 in the manipulation input unit illustrated in FIGS. 3A and 3B, and when the variable magnetic field button 91 is pressed as indicated by an arrow Y6 (see FIG. 3B), variable magnetic field instructing information for instructing generation of a variable magnetic field is input to the control unit 4. While the variable magnetic field instructing information is input, the magnetic field controller 43 generates a variable magnetic field for moving the capsule endoscope 10 restricted on a liquid surface into a liquid in the magnetic field generating unit 2.

Figure 5A:
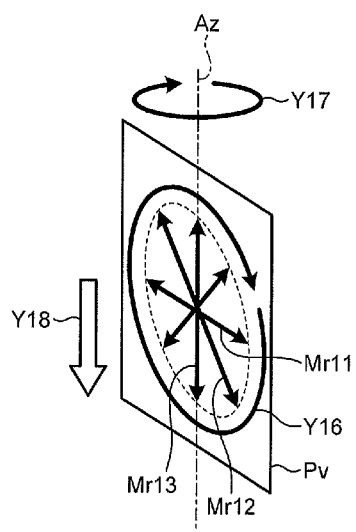
FIGS. 5A and 5B illustrate views of a variable magnetic field generated by a magnetic field generating unit illustrated in FIG. 1.
Figure 5B:
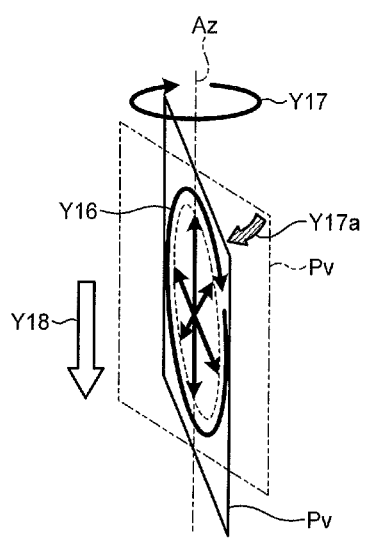

The variable magnetic field will be described with reference to FIGS. 5A and 5B. FIGS. 5A and 5B illustrate views of a variable magnetic field generated by the magnetic field generating unit 2. As illustrated in FIGS. 5A and 5B, the variable magnetic field includes a rotating magnetic field where a direction of the magnetic field is rotated as indicated by the arrow Y16 on a plane Pv parallel to a vertical axis Az, and a magnetic field for generating a magnetic attracting force for moving the permanent magnet 19 in a downward direction of the vertical axis Az as indicated by an arrow Y18. The magnetic field rotating on the plane Pv is pivoted about the vertical axis Az while rotating. FIGS. 5A and 5B illustrate only a representative vector of the direction vector of the rotating magnetic field generated by the magnetic field generating unit. The rotating magnetic field is a magnetic field having an intensity, by which the capsule endoscope 10 can be moved, and a direction rotating about an arbitrary point of the plane Pv at a predetermined period as indicated by arrows Mr11, Mr12, and Mr13. Further, the magnetic field for generating the magnetic attracting force in the vertically downward direction is set, for example, such that an intensity thereof becomes stronger toward a lower side from an upper side of the vertical axis Az.

Further, as indicated by an arrow Y17 of FIG. 5A, the magnetic field generating unit 2 generates a magnetic field such that the plane Pv is pivoted about the vertical axis Az at a predetermined period. For example, the plane Pv is pivoted about the vertical axis Az as indicated by an arrow Y17a of FIG. 5B until a predetermined time elapses from the state illustrated in FIG. 5A. Further, the pivot period of the plane Pv about the vertical axis Az is set to be sufficiently longer than a rotation period on the plane Pv of the rotating magnetic field so that the pivot of the plane Pv about the vertical axis Az does not influence the rotation of the rotating magnetic field.

Figure 6:
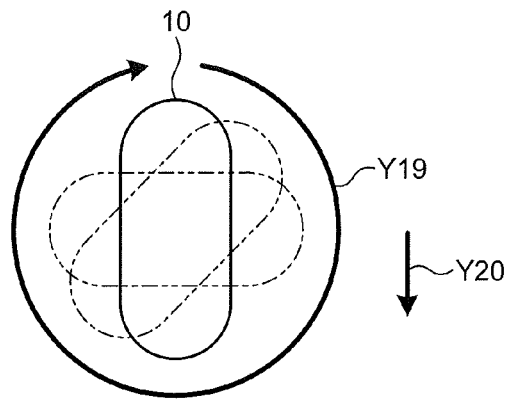
FIG. 6 is a view illustrating an operation of the capsule endoscope illustrated in FIG. 1 when a variable magnetic field is generated.

FIG. 6 is a view illustrating an operation of the capsule endoscope when a variable magnetic field is generated. FIG. 6 is a view where the capsule endoscope 10 is viewed from a direction perpendicular to the vertical axis Az. As the variable magnetic field is generated, on a plane parallel to the plane Pv, as indicated by an arrow Y19 illustrated in FIG. 6, a magnetic attracting force for rotating the capsule endoscope 10 about a center of the long axis of the capsule endoscope 10 and a magnetic attracting force for moving the capsule endoscope 10 vertically downward as indicated by an arrow Y20 are generated at the same time. For this reason, the capsule endoscope 10 is pulled vertically downward while rotating on a plane parallel to the plane Pv.

Further, as the plane Pv is pivoted about the vertical axis Az at a predetermined period, the rotation plane in which the capsule endoscope 10 is rotated is also pivoted about the vertical axis Az. Thus, as the capsule endoscope 10 is also pivoted about the vertical axis Az in response to the pivot of the rotation plane while rotating in a plane parallel to the plane Pv, a rotation direction of the capsule endoscope 10 is varied in response to the pivot of the rotation plane.

In this way, in the first embodiment, as the variable magnetic field is generated, the capsule endoscope 10 may be rotated in various directions, and thus the capsule endoscope 10 is apt to deviate from the restriction of a surface tension as compared with the case where a rotating operation is performed only in one direction.

Further, in the first embodiment, even when an obstacle such as a stomach wall exists, as a variable magnetic field is generated, the rotation plane in which the capsule endoscope 10 is rotated is periodically pivoted by itself, and thus when the rotation plane is rotated in a direction deviating from the obstacle, the capsule endoscope 10 may be moved in a direction where the capsule endoscope 10 is not hindered by the obstacle. For this reason, in the first embodiment, even when an obstacle exists, the capsule endoscope 10 may be moved in a direction deviating from the obstacle, and a problem in that the capsule endoscope 10 may be hampered by an obstacle so as not to perform a rotating operation and the capsule endoscope 10 may not be moved can be solved.

In addition, in the first embodiment, as the variable magnetic field is generated, the capsule endoscope 10 may be always pulled vertically downward while rotating toward various directions, and thus the capsule endoscope 10 can be released from the restriction of a surface tension of a liquid surface and be smoothly submerged into the liquid.

Furthermore, in the first embodiment, the movement of the capsule endoscope 10 is realized by combination of rotating magnetic fields of a power source having a low load, by which a magnetic field is smoothly varied, and thus a power source in the capsule medical device guiding system 1 can be miniaturized.

Further, in the capsule endoscope 10 in the first embodiment, the magnetization Ym of the permanent magnet 19 is parallel to the long axis La of the capsule endoscope 10, and the capsule endoscope 10 is rotated such that the direction of the long axis La coincides with the direction of the rotating magnetic field while the variable magnetic field is generated, and thus the capsule endoscope 10 is efficiently rotated with respect to the rotating magnetic field. For this reason, in the first embodiment, a marginal value of a magnetic field intensity of the rotating magnetic field may become small.

In addition, in the capsule medical device guiding system 1 according to the first embodiment, while the magnetic field generating unit 2 generates a variable magnetic field according to variable magnetic field instructing information, a purpose of selecting a variable magnetic field is displayed on the display unit 5, and thus a manipulator is notified of generation of a variable magnetic field.

Figure 7:
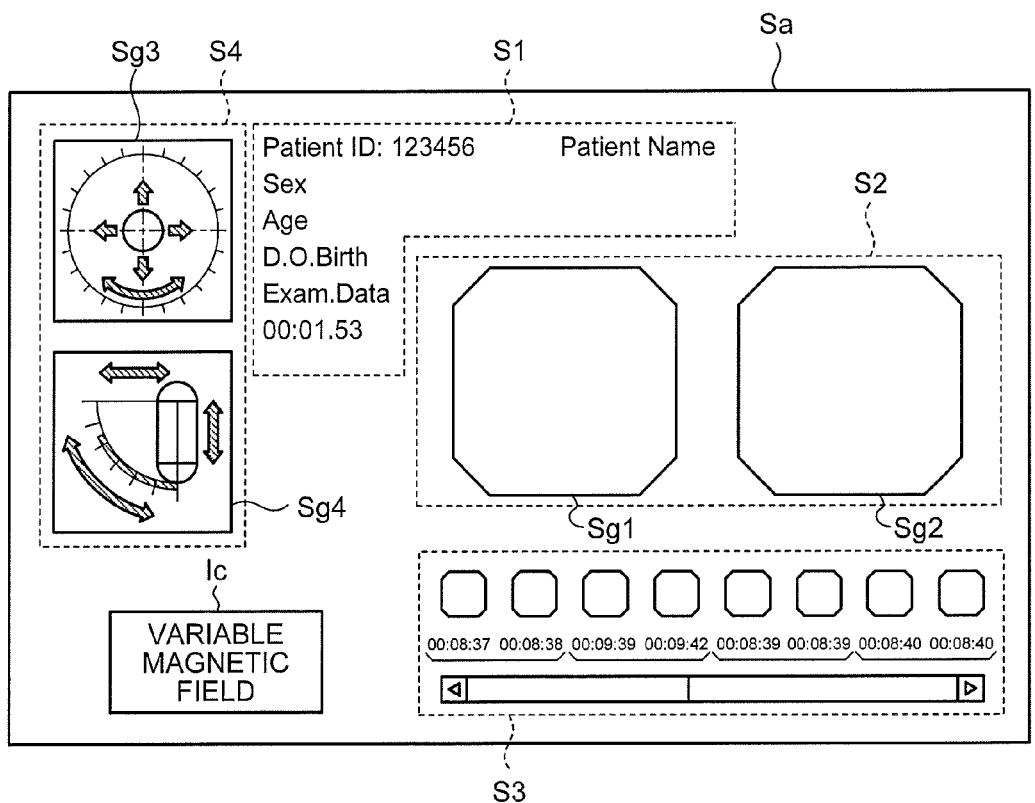
FIG. 7 is a view exemplifying a menu screen displayed on a display unit illustrated in FIG. 1.

For example, as illustrated in FIG. 7, the display unit 5 displays a menu Sa displaying a variable magnetic field icon Ic for notifying generation of a variable magnetic field on a left lower side, on the display screen. The variable magnetic field icon Ic is displayed by a bright color while the magnetic field generating unit 2 generates a variable magnetic field, and is displayed by a dark color while the magnetic field generating unit 2 stops generating a variable magnetic field.

Various subject information such as a patient name, a patient ID, a birth date, a gender, and an age of a subject is displayed in an area S1 on the left upper side of the menu Sa. In a central area S2 of the menu Sa, a living body image Sg1 captured by the imaging unit 11A is displayed on the left side and a living body image Sg2 captured by the imaging unit 11B is displayed on the right side. In an area S3 below the area S2 of the menu Sa, the captured images are reduced and displayed together with a capture time. In an area S4 on the left side of the menu Sa, a posture diagram Sg3 in a horizontal plane and a posture diagram Sg4 in a vertical plane are displayed as posture diagrams of the capsule endoscope 10. The postures of the capsule endoscope 10 displayed on the posture diagrams Sg3 and Sg4 display postures corresponding to guidance instructing information of the manipulation input unit 7. In the posture diagrams Sg3 and Sg4, a direction in which the capsule endoscope 10 can be guided is indicated by an arrow.

Figure 8:
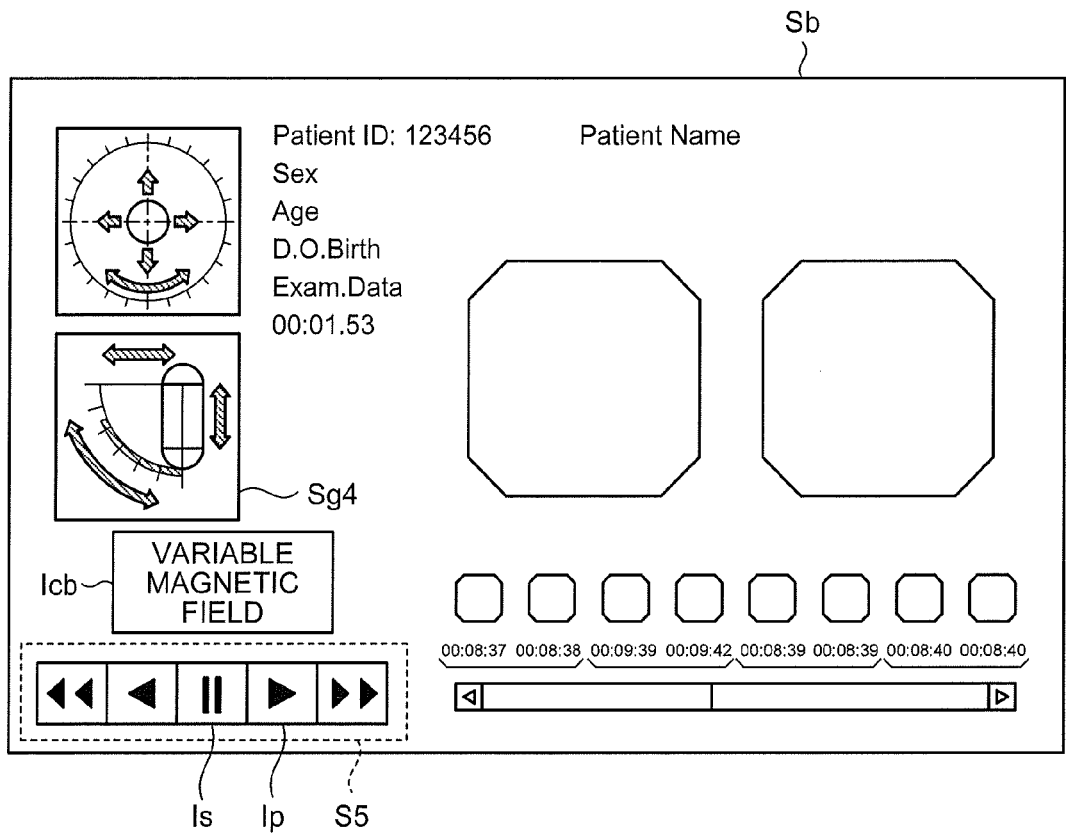
FIG. 8 is a view exemplifying a menu screen displayed on the display unit illustrated in FIG. 1.

Further, in the first embodiment, the generation states of the variable magnetic field during guidance of the capsule endoscope 10 may be preserved to correspond to the images, respectively. In this case, when an image is play backed after observation, it may be recognized whether the capsule endoscope 10 is guided with a variable magnetic field when the playback image is acquired, by displaying the variable magnetic field icon Icb representing generation of a variable magnetic field corresponding to the playback image on the left lower side of the menu Sb together with the playback image in the playback menu Sb (see FIG. 8). In addition, in an area S5 of the display menu Sb, an icon Ip for instructing playback of an image or an icon Is for temporary stop is displayed.

Further, in the first embodiment, although a rotating magnetic field for continuously rotating a direction of a magnetic field in the plane Pv parallel to the vertical axis Az has been described to be included as a variable magnetic field, as long as a rotating magnetic field capable of rotating the capsule endoscope 10 about a center of a long axis of the capsule endoscope 10 is included, a variable magnetic field including a direction varying magnetic field which periodically varies a direction of a magnetic field on a plane Pv may be used.

For example, as the direction varying magnetic field, in a plane Pv (see FIGS. 5A and 5B) parallel to the vertical axis Az, it is considered that a direction of a magnetic field having an intensity by which the capsule endoscope 10 is movable is changed to a direction of an arrow Mr11 (see FIGS. 5A and 5B) at a time t1, is changed to a direction of an arrow Mr12 (see FIGS. 5A and 5B) at a time t2 after lapse of a predeterminedtime from the time t1, and is changed to a direction of an arrow Mr13 (see FIGS. 5A and 5B) at a time t3 after lapse of a predetermined time from the time t2. When the magnetic field generating unit 2 generates the direction varying magnetic field, as an angle of the magnetic field direction on a plane is changed by a predetermined angle at an interval of a predetermined time, the capsule endoscope 10 may also be periodically rotated in a plane parallel to the plane Pv about a center of the long axis of the capsule endoscope 10 according to a direction of the changed magnetic field. Thus, in the first embodiment, by generating a variable magnetic field including a direction varying magnetic field for periodically changing a direction of a magnetic field in the plane Pv pivoting about the vertical axis Az, an angle between the long axis La of the capsule endoscope 10 and the vertical axis Az can be periodically changed and an angle between a reference plane (for example, a plane located in the plane Pv illustrated in FIG. 5A) passing through the vertical axis Az and a plane through which the long axis La of the capsule endoscope 10 and the vertical axis Az pass can also be periodically changed.

Further, in the first embodiment, although a case of pivoting the plane Pv which is a rotation plane of a rotating magnetic field about the vertical axis Az at a predetermined period has been described as an example, it is sufficient only if a rotating direction of the capsule endoscope 10 may be changed, and thus a direction of the plane Pv may be only periodically changed about the vertical axis even without continuously pivoting the plane Pv.

Figure 9:
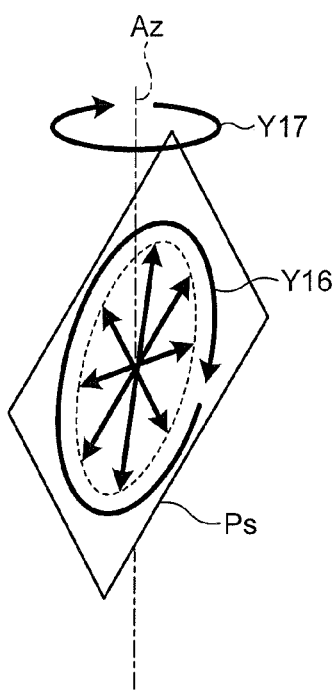
FIG. 9 illustrates a view of another example of a variable magnetic field generated by the magnetic field generating unit illustrated in FIG. 1.

Further, in the first embodiment, it is sufficient only if the capsule endoscope 10 is operated such that one end of the capsule endoscope 10 faces a direction close to a vertically lower side to submerge the capsule endoscope 10 in the liquid, and thus a rotation plane of the rotating magnetic field may be a plane other the horizontal plane. Thus, for example, the plane Ps which is a plane crossing the vertical axis Az illustrated in FIG. 9 may be set to the rotation plane of the rotating magnetic field. As indicted by an arrow Y17, the plane Ps is also controlled by the magnetic field controller 43 such that a direction thereof is periodically changed about the vertical axis Az.

Further, in the first embodiment, although a rotating magnetic field where a direction of a magnetic field is rotated has been described as a direction varying magnetic field, the present invention is not limited thereto. It is sufficient only if the capsule endoscope 10 repeats a posture where at least the long axis La of the capsule endoscope 10 and the vertical axis Az are perpendicular to each other in a plane parallel to the plane Pv such that the capsule endoscope 10 is operated to be significantly swung about the vertical axis Az. As illustrated in FIG. 4, the magnetization Ym of the permanent magnet 19 is parallel to the long axis La of the capsule endoscope 10, and thus there is a need to generate a direction varying magnetic field having a timing facing at least the horizontal direction such that the capsule endoscope 10 takes a posture where the long axis La is perpendicular to the vertical axis Az. Thus, in the first embodiment, it is sufficient only if a magnetic field for changing a direction of a magnetic field to a plurality of directions containing at least the horizontal direction is set as a direction varying magnetic field. That is, it is sufficient only if a direction varying magnetic field is set to contain a magnetic field facing 0° or 180° with reference to the vertically upward direction.

Figure 10:
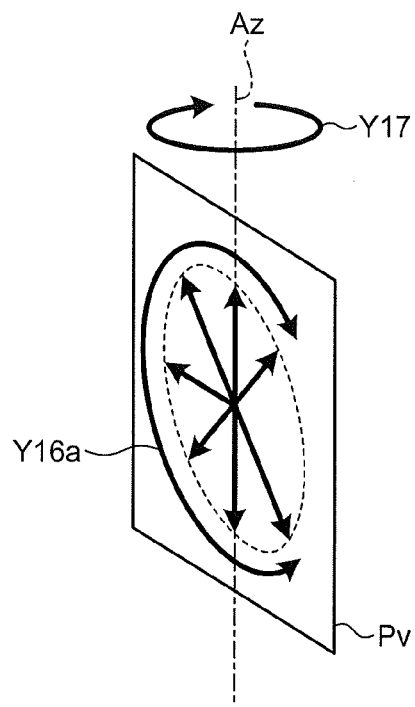
FIG. 10 illustrates a view of another example of a variable magnetic field generated by the magnetic field generating unit illustrated in FIG. 1.
Figure 11:
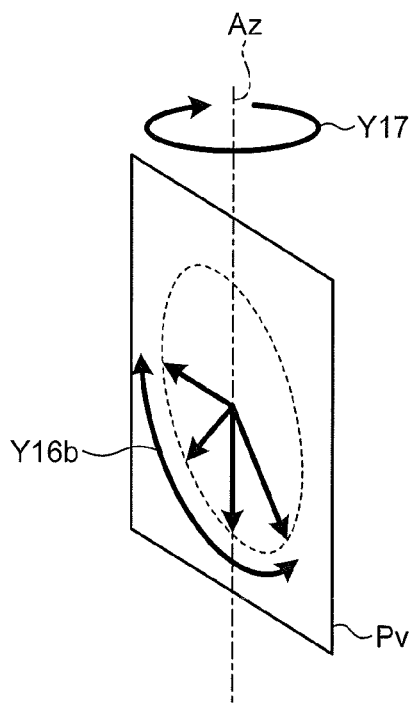
FIG. 11 illustrates a view of another example of a variable magnetic field generated by the magnetic field generating unit illustrated in FIG. 1.
Figure 12:
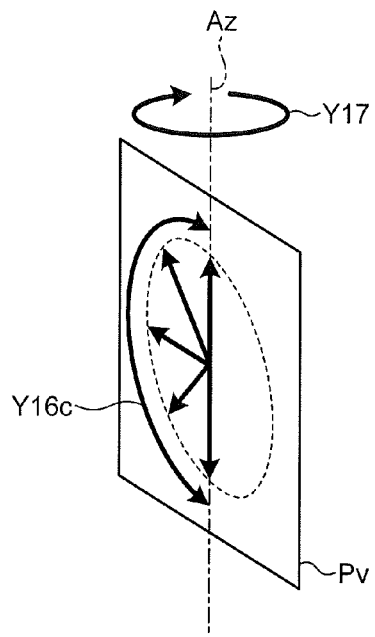
FIG. 12 illustrates a view of another example of a variable magnetic field generated by the magnetic field generating unit illustrated in FIG. 1.

A case of taking the counterclockwise direction as a positive direction with reference (0°) to the vertically upward direction will be described. For example, a direction of a magnetic field as the direction varying magnetic field may be set to be changed to the clockwise direction or the counterclockwise direction such that, as indicated by an arrow Y16a of FIG. 10, the direction of the magnetic field forms an angle of −45° to 225° with respect to the vertical axis Az. For example, a direction of a magnetic field may be set to be changed to the clockwise direction or the counterclockwise direction such that, as indicated by an arrow Y16b of FIG. 11, the direction of the magnetic field forms an angle of 90° to 225° with respect to the vertical axis Az. For example, a direction of a magnetic field may be set to be changed to the clockwise direction or the counterclockwise direction such that, as indicated by an arrow Y16c of FIG. 12, the direction of the magnetic field forms an angle of 0° to 180° with respect to the vertical axis Az. As a variable magnetic field including the direction varying magnetic field is generated, a magnetic attracting force by which an angle between the long axis La and the vertical axis Az of the capsule endoscope 10 is equal to or larger than 90° may be generated, and the capsule endoscope 10 may be released from the restriction of the surface tension while being significantly shaken about the vertical axis Az.

Figure 13:
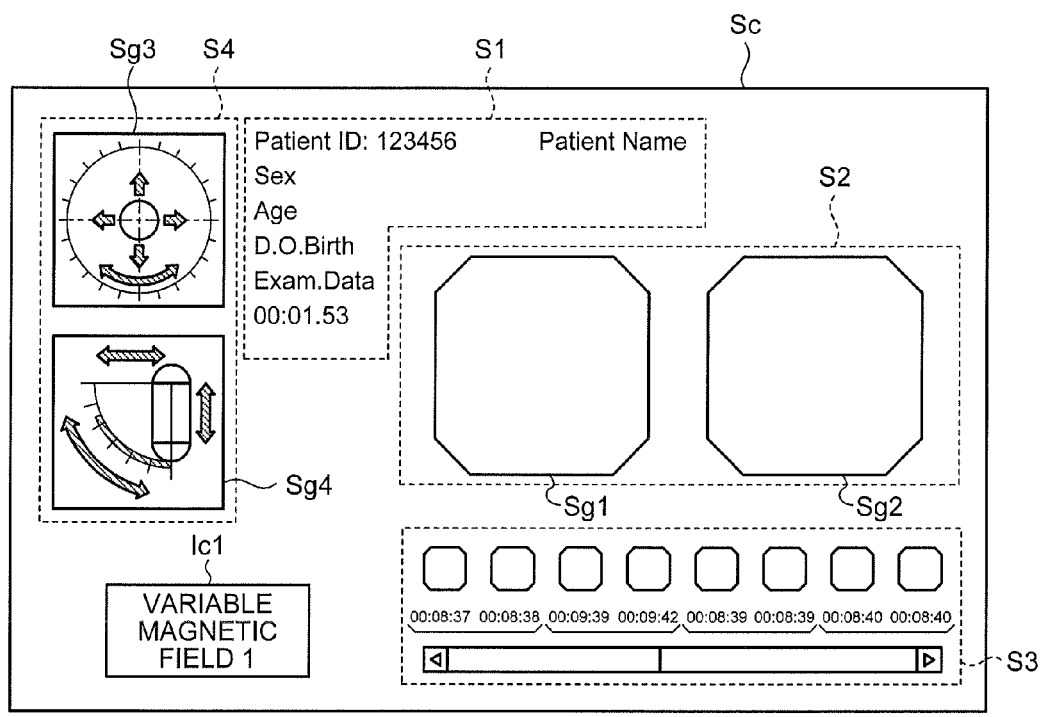
FIG. 13 is a view exemplifying a menu screen displayed on the display unit illustrated in FIG. 1.

Further, in the first embodiment, a desired variable magnetic field may be selected from a plurality of variable magnetic fields including the above-described direction varying magnetic fields. For example, when two variable magnetic fields are set, the manipulator may select a desired variable magnetic field from the two variable magnetic fields through manipulation of the input unit 6. In addition, the type of the selected variable magnetic field is displayed in a variable magnetic field icon Ic1 of the menu Sc illustrated in FIG. 13. Furthermore, the variable magnetic field icon Ic1 of FIG. 13 exemplifies a case of selecting a variable magnetic field 1 when the variable magnetic field 1 and a variable magnetic field 2 are set. When the variable magnetic field 2 is selected, the display of the variable magnetic field icon Ic1 is changed to a display where the variable magnetic field 2 is displayed.

Further, in the first embodiment, a magnetic attracting force for moving the capsule endoscope 10 vertically downward may become small as compared with the case where a density of the capsule endoscope 10 is smaller than a density of the liquid W introduced into the subject, by setting the density of the capsule endoscope 10 to be substantially the same as the density of the liquid W. In this case, an amount of energy supplied to generate a magnetic field in the magnetic field generating unit 2 becomes small and a load of the power source of the capsule medical device guiding system 1 becomes lower, and thus the power source can be miniaturized.

Second Embodiment

Next, a second embodiment will be described. In the second embodiment, a case of using a capsule endoscope having a magnetization in a direction crossing a long axis of the capsule endoscope will be described.

Figure 14:
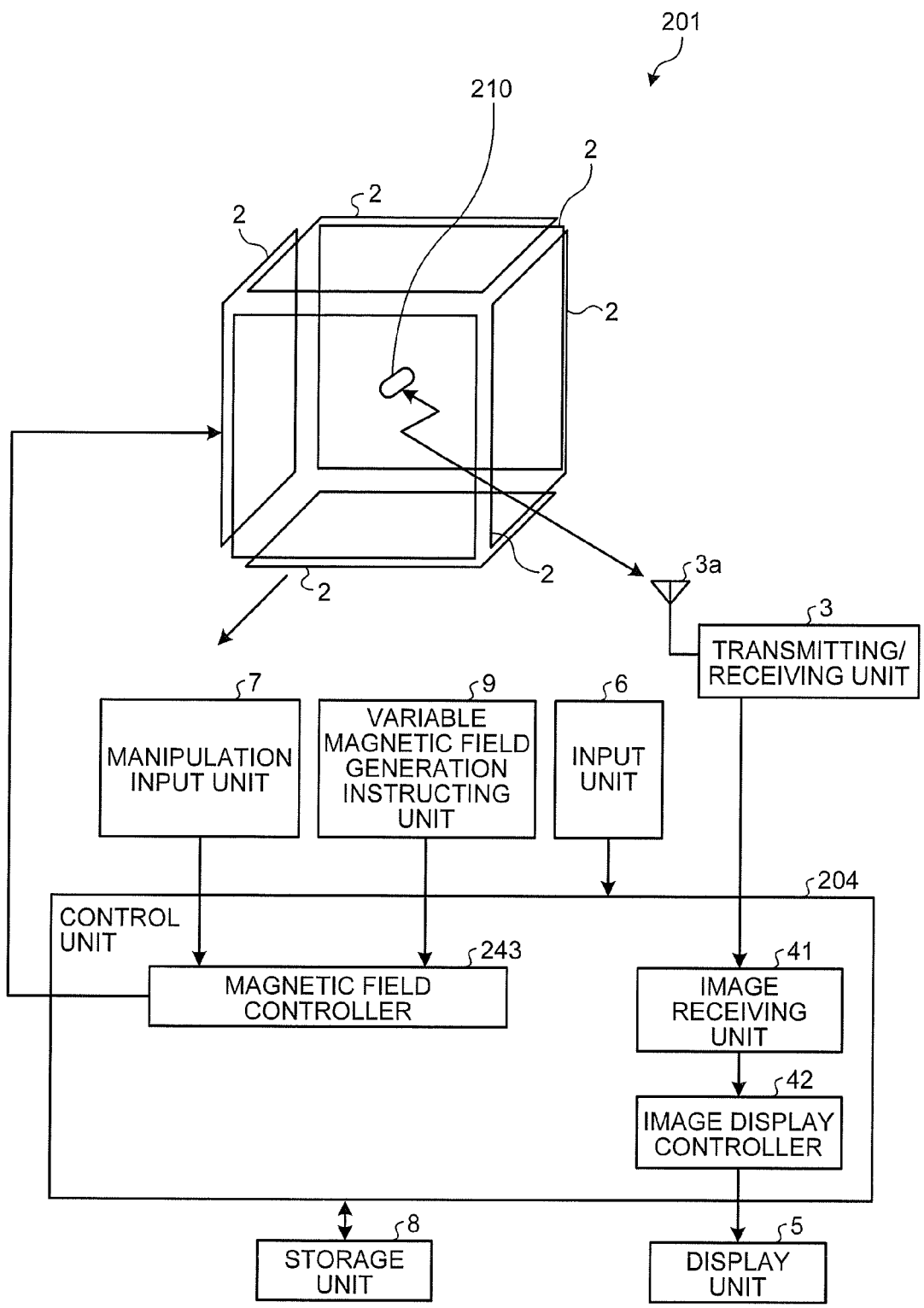
FIG. 14 is a schematic diagram illustrating an entire configuration of a capsule medical device guiding system according to a second embodiment.

FIG. 14 is a schematic diagram illustrating an entire configuration of a capsule medical device guiding system according to the second embodiment. As illustrated in FIG. 14, a capsule medical device guiding system 201 according to the second embodiment employs a capsule endoscope 210 instead of the capsule endoscope 10 illustrated in FIG. 1. The capsule medical device guiding system 201 according to the second embodiment has a control unit 204 instead of the control unit 4 illustrated in FIG. 1. The control unit 204 has a magnetic field controller 243 for controlling the magnetic field generating unit 2 to generate a magnetic field for guidance including a variable magnetic field corresponding to the capsule endoscope 210. Further, the capsule medical device guiding system 201 has the same manipulation input unit as the manipulation input unit illustrated in FIGS. 3A and 3B, and inputs guidance instructing information and the like to the control unit 204 from the manipulation input unit.

Figure 15:
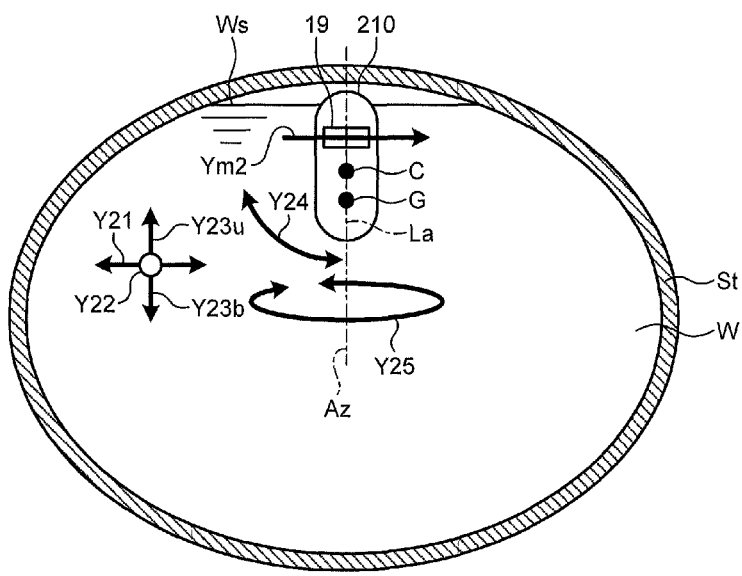
FIG. 15 is a view illustrating magnetization of a permanent magnet of a capsule endoscope illustrated in FIG. 14 and an operation of the capsule endoscope.

As illustrated in FIG. 15, in the capsule endoscope 210, a permanent magnet 19 is fixedly disposed to have a magnetization Ym2 in a direction perpendicular to the long axis La of the capsule endoscope 210. Further, a gravity center location G of the capsule endoscope 210 is set to a location moved in a direction different from the magnetization Ym2 of the permanent magnet 19 from a geometric center C of the capsule endoscope 210, and a direction of the long axis of the capsule endoscope 210 may be controlled according to a change in a direction of a magnetic field in the liquid W. For example, as illustrated in FIG. 15, the gravity center location G of the capsule endoscope 210 deviates from the long axis La of the capsule endoscope 210 from the geometric center C of the capsule endoscope 210 by adjusting disposition of the constituent elements of the capsule endoscope 210 such as a power source 18 and the permanent magnet 19.

As a result, a magnetic field for guiding the capsule endoscope 210 as indicated by the arrows of FIG. 15 is generated from the magnetic field generating unit 2, by manipulating the joysticks 71 and 72 (see FIGS. 3A and 3B), the up button 73U (see FIGS. 3A and 3B), and the down button 73B (see FIGS. 3A and 3B). Further, as in the first embodiment, when the joystick 71 is tilted as indicated by the arrow Y1 illustrated in FIG. 3A, the capsule endoscope 210 is guided to the left and right sides of the paper of FIG. 15 as indicated by the arrow Y21 of FIG. 15. When the joystick 71 is tilted as indicated by the arrow Y2 illustrated in FIG. 3A, the capsule endoscope 210 is guided in a direction perpendicular to the paper of FIG. 15. For example, when the capsule endoscope 210 is located on a point Y22 (see FIG. 15), the capsule endoscope 210 is guided in a direction perpendicular to the paper of FIG. 15 to pass through the point Y22. When the up button 73U is pressed as indicated by the arrow Y3u illustrated in FIG. 3B, the capsule endoscope 210 is guided vertically upward as indicated by an arrow Y23u of FIG. 15. When the down button 73B is pressed as indicated by the arrow Y3b of FIGS. 3A and 3B, the capsule endoscope 210 is guided vertically downward as indicated by an arrow Y23b of FIG. 15. Further, when the joystick 72 is tilted as indicated by the arrow Y4 illustrated in FIG. 3A, an end of the capsule endoscope 210 is guided such that a neck is shaken to the upper and lower sides of the paper as indicated by an arrow Y24 of FIG. 15. When the joystick 72 is tilted as indicated by the arrow Y5 illustrated in FIG. 3A, the capsule endoscope 210 is rotated about the vertical axis Az as indicated by an arrow Y25 of FIG. 15.

Figure 16A:
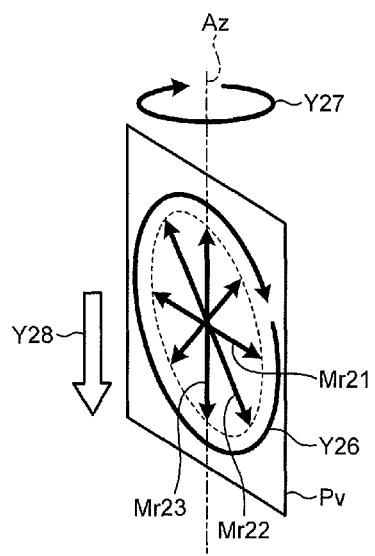
FIGS. 16A and 16B illustrate views of a variable magnetic field generated by a magnetic field generating unit illustrated in FIG. 14.
Figure 16B:
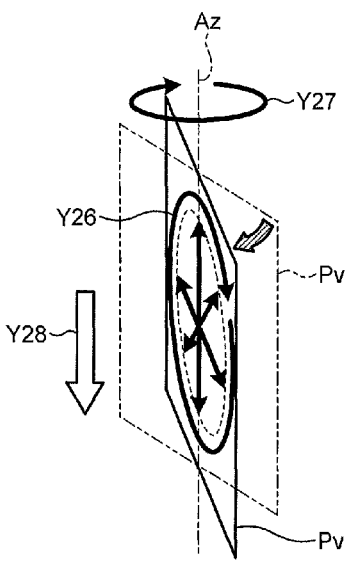

While the variable magnetic field button 91 illustrated in FIGS. 3A and 3B, is pressed, the magnetic field controller 243 generates a variable magnetic field for moving the capsule endoscope 210 restricted on a liquid surface into a liquid in the magnetic field generating unit 2. As illustrated in FIGS. 16A and 16B, the variable magnetic field generated at this time is the same as that of the first embodiment. That is, in the plane Pv pivoting about the vertical axis Az at a predetermined period as indicated by an arrow Y27, the variable magnetic field includes a rotating magnetic field where a direction of a magnetic field is rotated to the arrows Mr21, Mr22, and Mr23 at a predetermined period as indicated by an arrow Y26, and a magnetic field for generating a magnetic attracting force for moving the permanent magnet 19 to a lower side of the vertical axis Az as indicated by an arrow Y28. Further, as in the first embodiment, the rotating magnetic field has an intensity by which the capsule endoscope 210 can be moved, and the pivot period of the plane Pv about the vertical axis is set to be sufficiently longer than the rotation period in the plane Pv of the rotating magnetic field.

Figure 17:
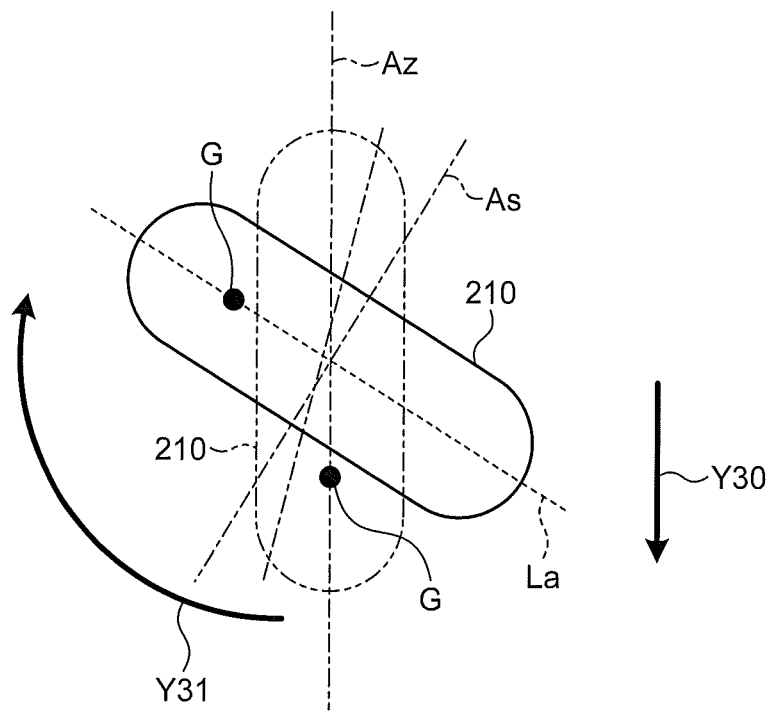
FIG. 17 is a view illustrating an operation of the capsule endoscope illustrated in FIG. 14 in the case where a rotation frequency of a rotating magnetic field is relatively low, when the capsule endoscope is viewed from a lateral side.
Figure 18:
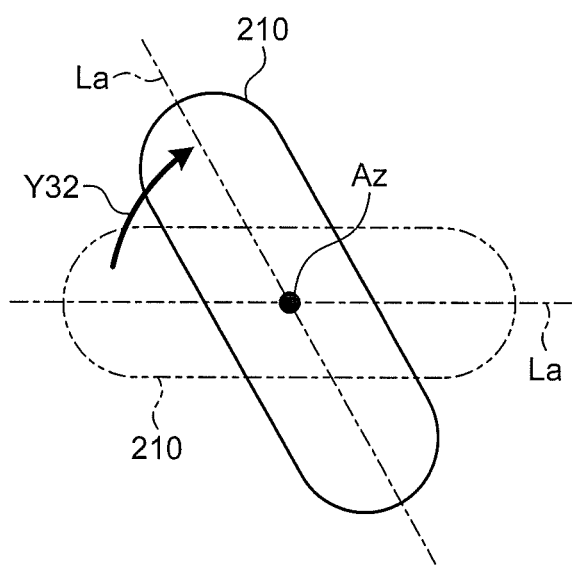
FIG. 18 is a view illustrating the capsule endoscope illustrated in FIG. 14 in the case where a rotation frequency of a rotating magnetic field is relatively low, when the capsule endoscope is viewed from an upper side.

In this case, an operation of the capsule endoscope 210 becomes different by the revolution per unit time (rotation frequency) of the rotating magnetic field in the variable magnetic field. A case where a rotation frequency of a rotating magnetic field is relatively low will be described with reference to FIGS. 17 and 18. FIG. 17 is a view illustrating the capsule endoscope 210 in the case where a rotation frequency of a rotating magnetic field is relatively low, when viewed from a direction perpendicular to the vertical axis. FIG. 18 is a view illustrating the capsule endoscope 210 in the case where a rotation frequency of a rotating magnetic field is relatively low, when viewed from a vertically upper side.

When a rotation frequency of a rotating magnetic field is relatively low, a vertically downward magnetic attracting force is always present as indicated by an arrow Y30 (see FIG. 17), and thus if a side where the gravity center G is located above the center as indicated by an arrow Y31 (see FIG. 17) as the rotating magnetic field is rotated, the side where the gravity center G is located falls down to the rear side of the paper toward a line As of FIG. 17. That is, when viewed from the upper side of the capsule endoscope 210, a direction of the long axis La of the capsule endoscope 210 is changed about the vertical axis Az as indicated by an arrow Y32 (see FIG. 18). Thereafter, in a plane parallel to the vertical axis Az passing through the long axis La whose direction has been changed, if the capsule endoscope 210 is rotated and the side where the gravity center G is located is on the upper side, an angle is changed to be tilted such that a direction of the long axis La is changed when viewed from the upper side. In this way, the capsule endoscope 210 repeats an operation of rotating in a plane parallel to the vertical axis Az while pivoting about the vertical axis Az as the side where the gravity center G is located is tilted.

Figure 19:
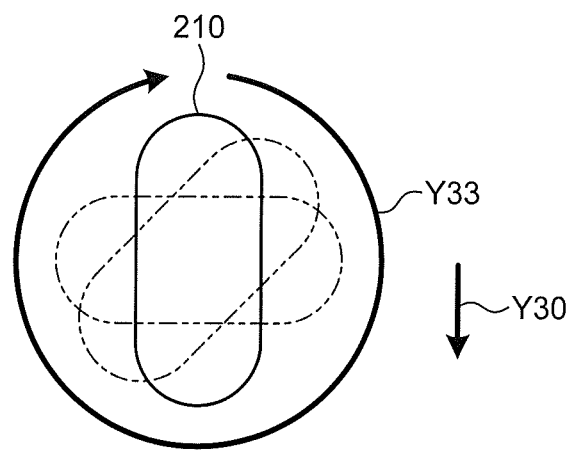
FIG. 19 is a view illustrating the capsule endoscope illustrated in FIG. 1 in the case where a rotation frequency of a rotating magnetic field is lower than 3 Hz, when the capsule endoscope is viewed from a lateral side.

A case where a rotation frequency of a rotating magnetic field is a predetermined frequency higher than the rotation frequency in the cases illustrated in FIGS. 17 and 18 will be described. For example, a case where a rotation frequency of the rotating magnetic field is lower than 3 Hz will be described. FIG. 19 is a view when the capsule endoscope 210 is viewed from a direction perpendicular to the vertical axis in the case where a rotation frequency of the rotating magnetic field is a frequency higher than the rotation frequencies of the cases illustrated in FIGS. 17 and 18 and lower than a predetermined frequency (for example, 3 Hz). In this case, a vertically downward magnetic attracting force is always present as indicated by an arrow Y30 (see FIG. 19) but the rotation of the rotating magnetic field is not slow such that the capsule endoscope 210 is tilted toward the center, and thus the capsule endoscope 210 can be rotated in a plane parallel to the plane Pv about the center of the long axis of the capsule endoscope 210 as indicated by an arrow Y33 (see FIG. 19). Further, a frequency where the capsule endoscope 210 can be rotated about the center of the long axis of the capsule endoscope 210 in a plane parallel to the plane Pv is determined by the shape, the mass, and the like of the capsule endoscope 210 and the density and the like of the liquid.

Figure 20:
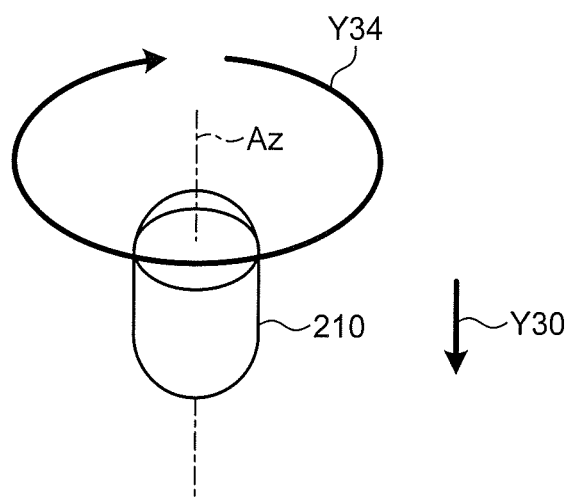
FIG. 20 is a view illustrating an operation of the capsule endoscope in the case where a rotation frequency of a rotating magnetic field is equal to or higher than 3 Hz, when the capsule endoscope is viewed from a lateral side.

A case where a rotation frequency of a rotating magnetic field is a frequency equal to or higher than 3 Hz which is higher than the rotation frequency in the case illustrated in FIG. 19 will be described. FIG. 20 is a view illustrating the capsule endoscope 210 in the case where a rotation frequency of a rotating magnetic field is equal to or higher than 3 Hz, when viewed from an upper side of the inclination. In this case, a rotation of the capsule endoscope 210 in the plane Pv is hampered by the liquid, and the capsule endoscope 210 is only rotated about the center of the vertical axis Az while being inclined as indicated by an arrow Y34 of FIG. 20.

Thus, in order to rotate the capsule endoscope 210 through the rotation as illustrated in FIG. 19, the rotation frequency of the rotating magnetic field has only to be optimized in correspondence to the capsule endoscope 210 and the liquid into which the capsule endoscope 210 is introduced. The rotation frequency of the rotating magnetic field is set according to the type of the capsule endoscope 210 and the type of the liquid, and is selected according to the capsule endoscope 210 or the liquid which is actually used. The rotation frequency of the rotating magnetic field is selected by selection information of the rotation frequency input from the input unit 6. Further, the rotation frequency of the rotating magnetic field may be minutely adjusted through manipulation of the input unit 6.

In this way, in the second embodiment, as a variable magnetic field including a rotating magnetic field a rotation frequency of which is optimized is generated, the capsule endoscope 210 can be always pulled vertically downward while rotating toward various directions, and thus the second embodiment shows the same effect as in the first embodiment.

Further, even in the second embodiment, a density of the capsule endoscope 210 may be set to be substantially the same as a density of the liquid W introduced into the subject such that a magnetic attracting force for moving the capsule endoscope 210 vertically downward becomes small.

In addition, even in the second embodiment, instead of a rotating magnetic field, the variable magnetic field may be set to include a direction varying magnetic field where a direction of a magnetic field is periodically changed on the plane Pv. Further, even in the second embodiment, a direction of the plane Pv which is a rotation plane may be periodically changed about the vertical axis Az, and the plane Pv may not necessarily pivot about the vertical axis Az.

Figure 21:
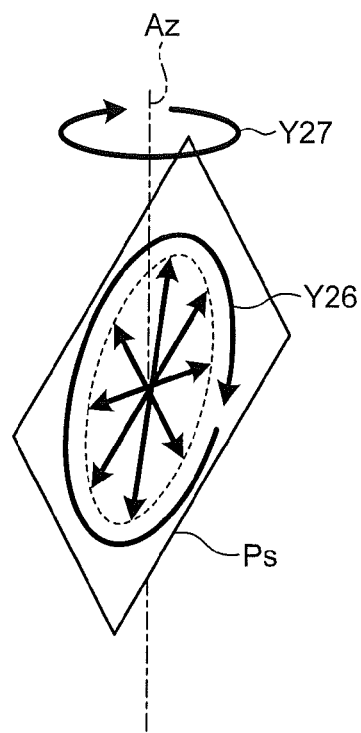
FIG. 21 illustrates a view of another example of a variable magnetic field generated by the magnetic field generating unit illustrated in FIG. 14.

Furthermore, in the second embodiment, it is sufficient only if the capsule endoscope 210 is operated such that a tip end of the capsule endoscope 210 faces a direction close to a vertically lower side to submerge the capsule endoscope 10 in the liquid, and thus a rotation plane of the rotating magnetic field may be a plane Ps (see FIG. 21) other the horizontal plane.

Further, in the second embodiment, it is sufficient only if the capsule endoscope 210 repeats a posture where at least the long axis La of the capsule endoscope 210 and the vertical axis Az are perpendicular to each other in a plane parallel to the plane Pv such that the capsule endoscope 10 is operated to be significantly shaken about the vertical axis Az. As illustrated in FIG. 15, the magnetization Ym2 of the permanent magnet 19 is perpendicular to the long axis La of the capsule endoscope 210, and thus there is a need to generate a direction varying magnetic field having a timing facing at least the vertical direction such that the capsule endoscope 210 takes a posture where the long axis La is perpendicular to the vertical axis Az. Thus, in the second embodiment, it is sufficient only if a magnetic field for changing a direction of a magnetic field to a plurality of directions containing at least the vertical direction is set as a direction varying magnetic field. That is, it is sufficient only if a direction varying magnetic field is set to contain a magnetic field facing 90° or 270° with reference) (0°) to the vertically upward direction.

Figure 22:
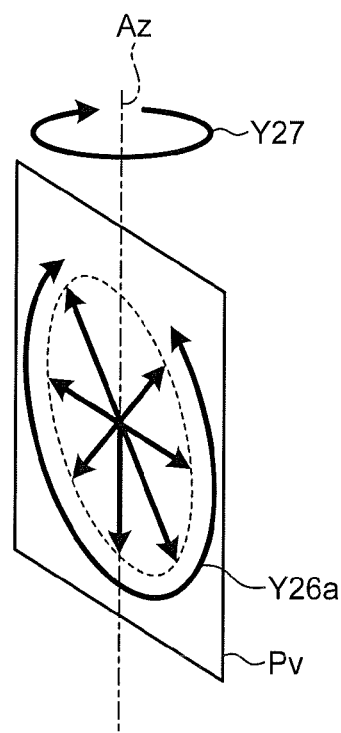
FIG. 22 illustrates a view of another example of a variable magnetic field generated by the magnetic field generating unit illustrated in FIG. 14.
Figure 23:
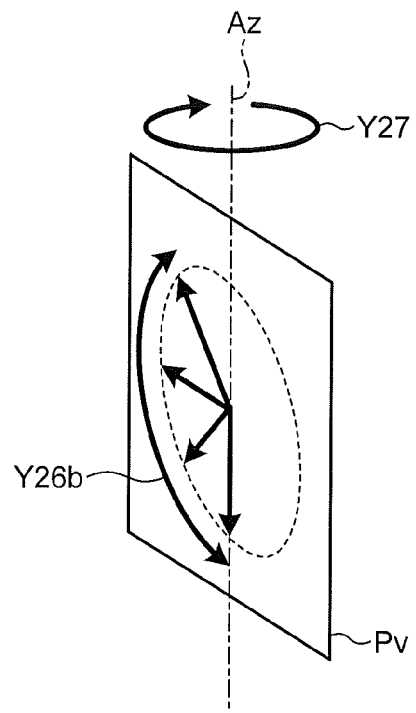
FIG. 23 illustrates a view of another example of a variable magnetic field generated by the magnetic field generating unit illustrated in FIG. 14.
Figure 24:
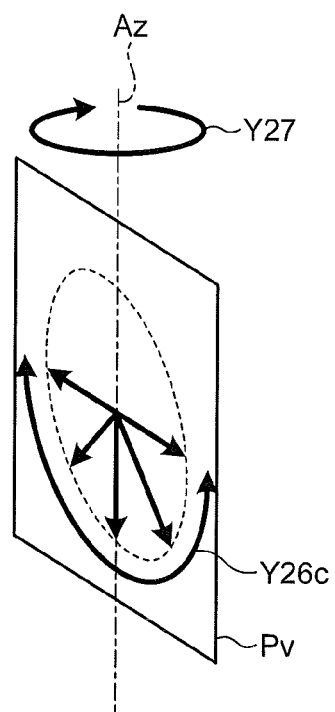
FIG. 24 illustrates a view of another example of a variable magnetic field generated by the magnetic field generating unit illustrated in FIG. 14.

A case of taking the counterclockwise direction as a positive direction with reference) (0°), to the vertically upward direction will be described. For example, a direction of a magnetic field as the direction varying magnetic field may be set to be changed to the clockwise direction or the counterclockwise direction such that, as indicated by an arrow Y26*a* of FIG. 22, the direction of the magnetic field forms an angle of 45° to 315° with respect to the vertical axis Az. For example, a direction of a magnetic field may be set to be changed to the clockwise direction or the counterclockwise direction such that, as indicated by an arrow Y26*b* of FIG. 23, the direction of the magnetic field forms an angle of 45° to 180° with respect to the vertical axis Az. For example, a direction of a magnetic field may be set to be changed to the clockwise direction or the counterclockwise direction such that, as indicated by an arrow Y26*c* of FIG. 24, the direction of the magnetic field forms an angle of 90° to 270° with respect to the vertical axis Az. As a variable magnetic field including the direction varying magnetic field is generated, a magnetic attracting force by which an angle between the long axis La and the vertical axis Az of the capsule endoscope 210 is equal to or larger than 90° may be generated, and the capsule endoscope 210 may be released from the restriction of the surface tension while being significantly shaken about the vertical axis.

Further, in the second embodiment, although the capsule endoscope 210 having a magnetization perpendicular to the long axis of the capsule endoscope has been described as an example, it is apparent that the present invention is not limited thereto and the permanent magnet 19 in the capsule endoscope may have a magnetization in a direction crossing the long axis of the capsule endoscope. Even the capsule endoscope can be rotated in correspondence to the rotation of a rotating magnetic field in a rotation plane of the rotating magnetic field included in the variable magnetic field by setting the center location of the capsule endoscope to a location moved in a direction different from the magnetization of the permanent magnet 19 from the geometric center of the capsule endoscope.

Figure 25:
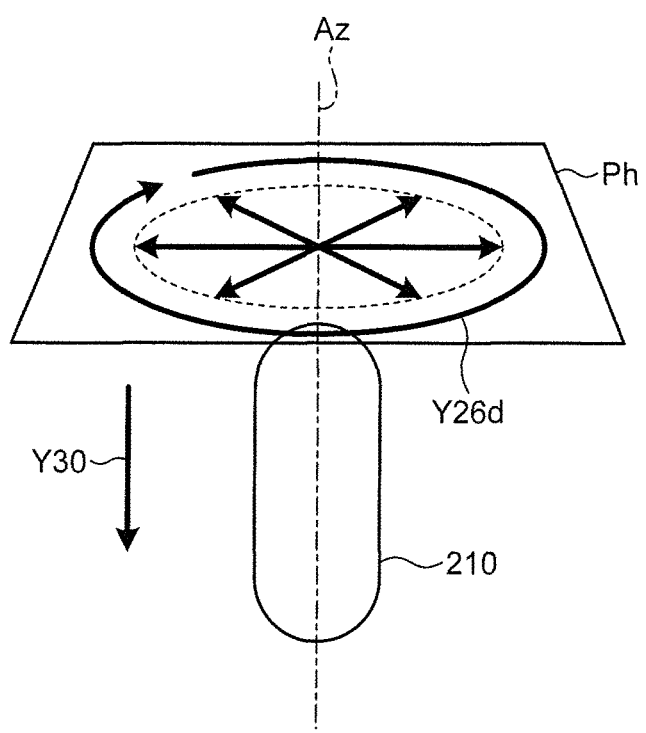
FIG. 25 illustrates a view of another example of a variable magnetic field generated by the magnetic field generating unit illustrated in FIG. 14.

In addition, in the second embodiment, although the rotating magnetic field included in the variable magnetic field has been described while taking a case of rotation in a plane other than the horizontal plane as an example, it is apparent that the rotation may be made in a horizontal plane Ph as illustrated in FIG. 25. In this case, the capsule endoscope 210 may deviate from the liquid while excluding a surface tension to rotate the horizontal plane Ph while the capsule endoscope 210 is always pulled as indicated by the arrow Y30 by a vertically downward magnetic attracting force.

Furthermore, in the first and second embodiments, although a case of using the capsule endoscopes 10 and 210 having a plurality of imaging units has been described as an example, it is apparent that a monocular capsule endoscope having only the first imaging unit 11A may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device guiding system, comprising:
   a capsule medical device including a permanent magnet and introduced into a liquid in a subject;
   a magnetic field generating unit configured to generate a magnetic field applied to the permanent magnet to guide the capsule medical device, and change a direction of the generated magnetic field in a three-dimensional space;
   a control unit configured to control the magnetic field to be generated by the magnetic field generating unit;
   a first manipulation input unit configured to instruct the control unit to apply a single magnetic field; and
   a second manipulation input unit configured to instruct the control unit to apply first and second magnetic fields simultaneously,
   wherein the control unit controls the magnetic field generating unit to generate the single magnetic field in response to instructions from the first manipulation input unit, and in a state where the capsule medical device is located on a liquid surface of the liquid, the control unit causes the first magnetic field to be generated such that a plane, which is parallel to a vertical axis and in which a magnetic field including a rotating magnetic field where a magnetic field is rotated on the plane is generated, pivots about the vertical axis at a predetermined period, and causes the second magnetic field to be generated for generating a magnetic attracting force for moving the permanent magnet vertically downward to submerge the capsule medical device in the liquid, and controls the first and second magnetic fields to be applied simultaneously, in response to instructions from the second manipulation input unit.

2. The capsule medical device guiding system according to claim 1, wherein the first magnetic field periodically changes each of an angle, which is between a long axis of the capsule medical device and the vertical axis, and an angle, which is between a predetermined reference plane passing through the vertical axis and a plane passing through the long axis of the capsule medical device and the vertical axis.

3. The capsule medical device guiding system according to claim 1, wherein the first magnetic field generates a magnetic field which makes an angle between a long axis of the capsule medical device and the vertical axis equal to or larger than 90°.

4. The capsule medical device guiding system according to claim 1, wherein the capsule medical device is moved in a liquid introduced into the subject, and has substantially a same density as a density of the liquid introduced into the subject.

5. The capsule medical device guiding system according to claim 4, wherein the permanent magnet has a magnetization in a direction parallel to a long axis of the capsule medical device.

6. The capsule medical device guiding system according to claim 4, wherein
   the permanent magnet has a magnetization in a direction crossing a long axis of the capsule medical device, and
   a gravity center location of the capsule medical device is a location which is deviated from a geometric center of the capsule medical device in a direction different from the magnetization of the permanent magnet.

7. The capsule medical device guiding system according to claim 6, wherein the permanent magnet has a magnetization in a direction perpendicular to the long axis of the capsule medical device.

8. The capsule medical device guiding system according to claim 1, wherein a pivot period of the plane which is parallel to the vertical axis and pivots about the vertical axis is longer than a rotation period of the rotating magnetic field rotating on the plane.

9. A capsule medical device guiding system, comprising:
   a capsule medical device including a permanent magnet, introduced into a liquid of a subject, and having substantially a same density as a density of a liquid introduced into the subject;
   a magnetic field generating unit configured to generate a magnetic field applied to the permanent magnet to guide the capsule medical device, and change a direction of the generated magnetic field in a three-dimensional space; and
   a control unit configured to control the magnetic field to be generated by the magnetic field generating unit,
   wherein in a state where the capsule medical device is located on a liquid surface of the liquid, the control unit causes a first magnetic field to be generated such that a plane, which is parallel to a vertical axis, pivots about the vertical axis at a predetermined period under conditions that a magnetic field including a rotating magnetic field where a magnetic field is rotated on the plane is generated and the capsule medical device rotates about an axis perpendicular to a long axis of the capsule medical device, and causes a second magnetic field to be generated for generating a magnetic attracting force for moving the permanent magnet vertically downward to submerge the capsule medical device in the liquid, and controls the first and second magnetic fields to be applied simultaneously.

10. The capsule medical device guiding system according to claim 9, further comprising:
    a first manipulation input unit configured to instruct the control unit to apply a single magnetic field; and
    a second manipulation input unit configured to instruct the control unit to apply the first and second magnetic fields simultaneously.

11. A magnetic field generating device for generating a magnetic field for a capsule medical device including a permanent magnet, comprising:
    a magnetic field generating unit configured to generate a magnetic field applied to the permanent magnet to guide the capsule medical device, and change a direction of the generated magnetic field in a three-dimensional space; and
    a control unit configured to control the magnetic field to be generated by the magnetic field generating unit,
    wherein in a state where the capsule medical device is located on a liquid surface of the liquid, the control unit causes a first magnetic field to be generated such that a plane, which is parallel to a vertical axis, pivots about the vertical axis at a predetermined period under conditions that a magnetic field including a rotating magnetic field where a magnetic field is rotated on the plane is generated and the capsule medical device rotates about a center of a long axis of the capsule medical device, and causes a second magnetic field to be generated for generating a magnetic attracting force for moving the permanent magnet vertically downward to submerge the capsule medical device in the liquid, and controls the first and second magnetic fields to be applied simultaneously.

12. A capsule medical device guiding system, comprising:
    a capsule medical device including a permanent magnet and introduced into a liquid in a subject;
    a magnetic field generating unit configured to generate a magnetic field applied to the permanent magnet to guide the capsule medical device, and change a direction of the generated magnetic field in a three-dimensional space;
a control unit configured to control the magnetic field to be generated by the magnetic field generating unit;
a first manipulation input unit configured to instruct the control unit to apply a single magnetic field; and
a second manipulation input unit configured to instruct the control unit to apply first and second magnetic fields simultaneously,
wherein a gravity center of the capsule medical device is disposed at a location moved in a direction different from a magnetization direction of the permanent magnet from a geometric center of the capsule medical device, and
the control unit controls the magnetic field generating unit to generate the single magnetic field in response to instructions from the first manipulation input unit, and in a state where the capsule medical device is located on a liquid surface of the liquid, the control unit controls the magnetic field generating unit to simultaneously apply the first magnetic field, a direction of which is changed from a state where the gravity center of the capsule medical device is located below the geometric center with respect to a vertical direction to a state where the gravity center of the capsule medical device is located above the geometric center with respect to the vertical direction, and the second magnetic field for moving the permanent magnet downward along the vertical direction to generate a magnetic attracting force for submerging the capsule medical device into the liquid, in response to instructions from the second manipulation input unit.

13. The capsule medical device guiding system according to claim 12, wherein the control unit controls the magnetic field generating unit such that a direction of the first magnetic field is periodically changed on a plane other than a horizontal plane.

14. The capsule medical device guiding system according to claim 13, wherein the control unit controls the magnetic field generating unit such that a direction of the first magnetic field is rotated on a plane other than the horizontal plane.

15. The capsule medical device guiding system according to claim 14, wherein the control unit controls the magnetic field generating unit such that a frequency at which the first magnetic field is rotated on a plane other than the horizontal plane for changing a direction is lower than 3 Hz.

16. The capsule medical device guiding system according to claim 13, wherein the control unit controls the magnetic field generating unit such that a plane other than the horizontal plane where the first magnetic field changes a direction is periodically changed about the vertical axis.

17. The capsule medical device guiding system according to claim 16, wherein the control unit controls the magnetic field generating unit such that a period by which a direction of the first magnetic field is changed on a plane other than the horizontal plane is shorter than a period by which a plane other than the horizontal plane is changed about a vertical axis.

18. The capsule medical device guiding system according to claim 12, wherein the control unit releases restriction of the capsule medical device on a liquid surface of the liquid as the capsule medical device is tilted down to a state where the gravity center of the capsule medical device is located below the geometric center in the process of changing from a state where the gravity center of the capsule medical device is below the geometric center to a state where the gravity center of the capsule medical device is above the geometric center by the first magnetic field.

* * * * *